United States Patent [19]

Goegelman et al.

[11] 4,378,353

[45] Mar. 29, 1983

[54] NOVEL C-076 COMPOUNDS

[75] Inventors: Robert T. Goegelman, Linden; Vincent P. Gullo, Edison, both of N.J.; Louis Kaplan, New City, N.Y.

[73] Assignee: Merck & Co., Inc., Rahway, N.J.

[21] Appl. No.: 235,338

[22] Filed: Feb. 17, 1981

[51] Int. Cl.$^3$ .................... A61K 31/71; C07D 493/20
[52] U.S. Cl. .................................. 424/181; 536/7.1; 549/264; 424/279; 435/76; 435/119
[58] Field of Search ............. 536/4, 17 R, 17 C; 260/343.41; 424/181, 279

[56] References Cited

U.S. PATENT DOCUMENTS

| | | | |
|---|---|---|---|
| 3,950,360 | 4/1976 | Aoki et al. | 260/343.41 |
| 3,984,564 | 10/1976 | Aoki et al. | 260/343.41 |
| 4,134,973 | 1/1979 | Fisher et al. | 336/17 |
| 4,285,963 | 8/1981 | Arison et al. | 260/343.41 |

FOREIGN PATENT DOCUMENTS 1573955  4/1977  United Kingdom .

OTHER PUBLICATIONS

Tetrahedron Letters 10, pp. 711–714 (1975).

*Primary Examiner*—Jane T. Fan
*Attorney, Agent, or Firm*—David L. Rose; Mario A. Monaco

[57] ABSTRACT

There are disclosed certain new compounds related to C-076 compounds which have been produced by a mutant of the culture that produced the original C-076 compounds and isolated from the fermentation broth thereof. The compounds retain the C-076 16-membered cyclic backbone, however, the groups attached thereto are considerably modified from the original C-076 compounds. The new compounds have been found to retain the biological activity of the parent C-076 compounds. The compounds are thus potent antiparasitic agents and compositions and methods for such uses are also disclosed.

11 Claims, No Drawings

NOVEL C-076 COMPOUNDS

BACKGROUND OF THE INVENTION

The C-076 family of compounds are a series of macrolides isolated from the fermentation broth of a strain of *Streptomyces avermitilis*. The C-076 compounds are characterized by having a 16-membered cyclic backbone substituted with a disaccharide and having a bicyclic spiroketal fused thereon. The compounds have the structure:

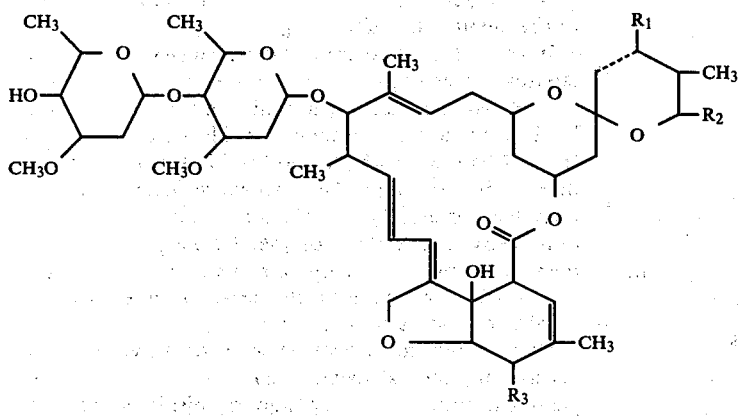

wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

The C-076 compounds are named using a system of designations which corresponds to the structural variations as is set forth in the following table.

| Compound | $R_1$        | $R_2$      | $R_3$   |
|----------|--------------|------------|---------|
| A1a      | Double bond  | sec-butyl  | —OCH₃   |
| A1b      | Double bond  | iso-propyl | —OCH₃   |
| A2a      | —OH          | sec-butyl  | —OCH₃   |
| A2b      | —OH          | iso-propyl | —OCH₃   |
| B1a      | Double bond  | sec-butyl  | —OH     |
| B1b      | Double bond  | iso-propyl | —OH     |
| B2a      | —OH          | sec-butyl  | —OH     |
| B2b      | —OH          | iso-propyl | —OH     |

The above compounds are isolated from the fermentation broth of *Streptomyces avermitilis* using normal extraction and isolation procedures. The C-076 producing culture and the morphological characteristics thereof along with the procedures used for separating and isolating the C-076 compounds, are fully described in Great Britain Pat. No. 157/3955, published Aug. 28, 1980.

The fermentation is carried out in an aqueous medium and includes an assimilable source of carbon, an assimilable source of nitrogen and inorganic salts and the fermentation is generally carried out under aerobic conditions. The specific nutrients and parameters for the fermentation are described completely in the above cited Great Britain Patent.

The C-076 producing culture and a mutant thereof have been deposited in the permanent culture collection of the American Type Culture Collection, 12301 Parklawn Drive, Rockville, Maryland 20852. The cultures are accessible under the accession numbers ATCC 31267 for the basic culture and ATCC 31272 (lyophilized tube) and ATCC 31271 (frozen vial) for the mutant. The C-076 compounds are potent antiparasitic agents with very broad spectrum anthelmintic, acaricidal, nematocidal and insecticidal activity.

SUMMARY OF THE INVENTION

The instant invention is concerned with novel C-076 derivatives and procedures for their isolation from the fermentation broth of a C-076 producing mutant strain of *Streptomyces avermitilis*. Thus, it is an object of this invention to describe such novel C-076 derivatives. A further object is to describe the mutant strain of *Streptomyces avermitilis*, MA-5218. It is a further object of this invention to describe the processes for their isolation from fermentation broths. A still further object is to describe the anti-parasitic effects of such novel compounds. Further objects will become apparent from a reading of the following description.

DESCRIPTION OF THE INVENTION

The novel compounds of this invention are best described in the following three structural formulae:

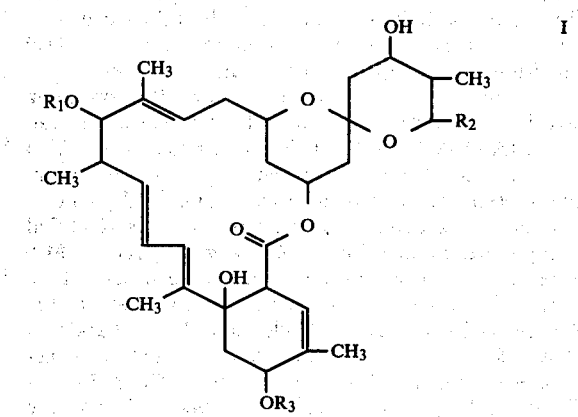

wherein (a) $R_1$ is α-L-oleandrosyl; $R_2$ is sec. butyl; and $R_3$ is methyl;

(b) $R_1$ is α-L-oleandrosyl; $R_2$ is sec. butyl; and $R_3$ is hydrogen.

(c) $R_1$ is α-L-oleandrosyl-α-L-oleandrosyl; $R_2$ is sec. butyl and $R_3$ is hydrogen.

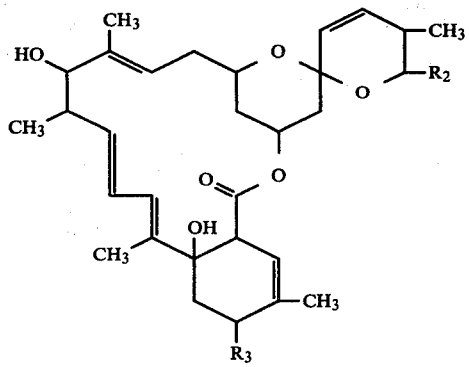

II wherein
(a) $R_2$ is iso-propyl; and $R_3$ is methoxy;
(b) $R_2$ is sec-butyl; and $R_3$ is keto;
(c) $R_2$ is iso-propyl; and $R_3$ is keto;

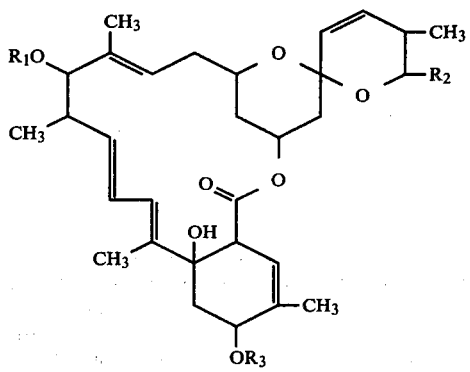

III wherein $R_1$ is α-L-oleandrosyl-α-L-oleandrosyl; $R_2$ is sec-butyl; and $R_3$ is hydrogen.

From an analysis of the foregoing seven compounds, they are seen to be similar to the parent C-076 compounds, but with some very major differences.

In all of the structures, I to III above, the C-076 furan ring has been opened. In addition, in structures I (a) and (b) and II (a), (b) and (c), one or both of the sugar moieties have been cleaved and, in compounds II (b) and (c) the 5-position group has been oxidized to a keto.

The mutant culture which produces the foregoing novel compounds was produced from the parent culture MA-4848 (ATCC 31272) in a procedure which involved the ultraviolet irradiation of a spore suspension thereof followed by agar medium growth and random colony selection. The mutant culture is identified in the culture collection of Merck & Co., Inc. as MA 5218 and has been deposited without restriction as to availability in the permanent culture collection of the American Type Culture Collection, 12301 Parklawn Drive, Rockville, Maryland 20852. The culture is accessable under the accession number ATCC 31780.

Although a mutant, the culture MA 5218 has the same morphological characteristics as the parent culture from which it is derived except that it is blue-green in coloration rather than gray. The morphology of the cultures is described in detail in the above-cited British patent.

The C-076 derivatives are produced during the aerobic fermentation of suitable aqueous nutrient media under conditions described hereinafter, with a producing mutant strain of Streptomyces avermitilis. Aqueous media such as those used for the production of many antibiotic substances are suitable for use in this process for the preparation of these C-076 derivatives.

Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, sucrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen sources such as yeast hydrolysates, yeast autoysate, soybean meal, casein hydrolysates, yeast extracts, corn steep liquors, distillers solubles, cottonseed meal, meat extract and the like, are readily assimilable by Streptomyces avermitilis in the production of the C-076 compounds. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, magnesium, ammonium, calcium, phosphate, sulfate, chloride, carbonate and like ions. Also included are trace metals such as cobalt, manganese, iron and the like.

The growth media discussed in the above South African Patent are all suitable for the satisfactory growth of the instant mutant culture, however certain media have been found to be particularly suitable for the optimum growth of MA-5218. Examples of such preferred media are as follows:

| Ingredient | Content (%) |
| --- | --- |
| Medium A | |
| Acid-hydrolyzed casein (salt free-vitamin free) | 2% |
| Yeast extract | 2% |
| Glucose | 2% |
| $KNO_3$ | 0.2% |
| NaCl | 0.05% |
| $MgSO_4.7H_2O$ | 0.05% |
| $FeSO_4.7H_2O$ | 0.0025% |
| $MnSO_4.H_2O$ | 0.0005% |
| $ZnSO_4.7H_2O$ | 0.001% |
| $CaCl_2.2H_2O$ | 0.002% |
| pH - before sterilization | 7.0 |
| Medium B | |
| Peptonized milk | 1.0% |
| Autolyzed yeast, ardamine pH | 0.15% |
| Glucose | 4.5% |
| pH - before sterilization | 7.0 |
| Medium C | |
| Yeast Extract | 0.4% |
| Malt Extract | 1.0% |
| Glucose | 0.4% |
| Bacto agar | 2.0% |

| -continued | |
| --- | --- |
| Ingredient | Content (%) |
| pH - before sterilization | 7.0% |

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, *Ostertagia, Nematodirus, Cooperia, Ascaris*, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, perferably of the vegetable oil variety such as peanut oil, cotton seed oil and the like. Other parenteral vehicles such as organic preparation using solketal, glycerol, formal and aqueous parenteral formulations are also used. The active C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infection. Generally, good results are obtained with our novel compounds by the oral administration of from about 0.001 to 10 mg. per kg. of animal body weight, such total dose being given at one time or in divided doses over a relatively short period of time such as 1-5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal edible bean mill feed, soya grits, crushed limestone and the like. The active C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 compound employed, the compounds of this invention are usually fed at concentrations of between 0.00001 to 0.002% in the feed order to achieve the desired antiparasitic result.

In using the compounds of this invention, the individual C-076 components may be isolated and purified and used in that form. Alternatively, mixtures more of the individual C-076 components may be used. It is not necessary to completely separate the various C-076 compounds obtained from the purification of the fermentation broth. Occasionally, there is obtained a mixture containing two or more of the C-076 compounds, but having other unrelated compounds excluded therefrom, and such mixture may be used for the prevention and treatment of parasitic diseases as described herein. Such a mixture generally will contain unequal proportions of the C-076 compounds, however, all of the compounds have substantial activity and the antiparasitic activity of the mixture can be accurately determined.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are isolated from the fermentation broth of *Streptomyces avermitilis* using procedures substantially similar to those used to isolate the parent C-076 compounds as is described in the above Great Britain patent. The standard techniques for extraction and purification, known to those skilled in the art, are employed to purify the instant compounds. The techniques of solvent extraction, column chromatography, thin layer chromatography, preparative layer chromatography, high pressure liquid chromatography and the like are useful for the isolation and purification of the instant compounds.

The following examples describe the fermentation and the isolation and purification procedures for the preparation of the instant compounds. The examples are provided in order that the invention might be more fully understood. They should not be construed as limitative of the invention.

EXAMPLE 1

Fermentation of *Streptomyces avermitilis* MA 5218

A 250 ml baffled Erlenmeyer flask containing 25 ml of Medium A (seed medium) is innoculated with a 5.0 mm plug from a petri plate containing the growth of *Streptomyces avermitilis* MA 5218 (ATCC 31780) in Medium C. The flask is incubated on a rotary shaker at 28° C. for 28 hours at 220 rpm.

This seed culture is used to inoculate seventeen 250 ml Erlenmeyer flasks containing 40 ml of Medium B each. The inoculum volume is 1.0 ml (2.5%). The flasks are incubated at 28° C. for 8 days at 220 rpm on a rotary shaker.

EXAMPLE 2

Isolation of Compounds from MA 5218

The fermentation broth, 575 ml, is filtered and the filtrate is discarded. The mycelia cake is extracted by stirring with 300 ml of acetone for one hour. The slurry is filtered and the wet filter cake washed with 100 ml of acetone yielding 400 ml of acetone extract. The acetone extract is concentrated to 75 ml and extracted three times with 25 ml of methylene chloride. The combined methylene chloride extracts are treated with 30 g of sodium sulfate and filtered. The filtrate is concentrated to 25 ml. Silica gel (7 g) is added to this solution and the remaining solvent is then removed. The coated silica gel is then placed onto a column containing 35 g of silica gel. The column is washed with 150 ml of methylene chloride and eluted with 275 ml of 20% methanol/methylene chloride. The eluate is concentrated to yield 1.70 g of a viscous oil. The 1.70 g is placed on eight preparative silica gel plates and the plates are developed with 15% isopropanol/hexane. Three bands are eluted containing the following quantities of material: 560 mg (Band A), 262 mg (Band B) and 70 mg (Band C).

The 560 mg sample (Band A) is dissolved in 50 ml of methylene chloride and filtered through 3 g of carbon. The filtrate is concentrated and yields 474 mg of oil. This material is placed on three preparative silica gel plates and the plates are developed three times with 5% isopropanol/hexane. Two bands are eluted containing 134 mg (Band D) and 166 mg (Band E) of material. The 134 mg of material, (Band D), is chromatographed on three preparative silica gel plates. The plates are developed two times with 5% ethyl acetate/methylene chloride. This yields a fraction containing 59.3 mg (Band G). The fraction is purified by high performance liquid chromatography using an ES Industries Chromega ® column ($C_{18}$) and elution with acetonitrile/methanol/water (62/18/20). This final purification yields 13.6 mg of Compound IIa. The 166 mg of material (Band E) is placed on two preparative silica gel plates and the plates are developed with 10% ethyl acetate/methylene chloride. One fraction is collected containing 121 mg of material (Band H). Preparative silica gel thin-layer chromatography of this material using two developments of 5% ethyl acetate/methylene chloride yields 94 mg of Band I. High performance liquid chromatography of this material yields two fractions containing 6.0 mg and 65.7 mg of material. The 6.0 mg sample is again purified on the high performance liquid chromatograph to yield 4.08 mg of Compound IIc. The 65.7 mg sample is crystallized from 1 ml of methanol to yield 41 mg of Compound IIb.

The 262 mg sample (Band B) is purified by high performance liquid chromatography using an ES Industries Chromega ® column ($C_{18}$) and elution with acetonitrile/methanol/water (62/18/20). This yields a 56.6 mg sample which is again purified by high performance liquid chromatography and elution with the solvent mixture of acetonitrile/methanol/water (56/28/26). This final purification yields 20.8 mg of Compound Ia.

The 70 mg sample (Band C) is placed on a preparative silica gel plate and the plate is developed two times with 35% ethyl acetate/methylene chloride. One band is eluted containing 36.4 mg (Band J) of material. This sample is fractionated by high performance liquid chromatography using an ES Industries Chromega ® column ($C_{18}$) and elution with acetonitrile/methanol/water (62/18/20). Three fractions are collected containing 7.77 mg of Compound Ic 1.66 mg of Compound III and 2.0 mg of impure Compound Ib. This latter sample is rechromatographed to yield 1.80 mg of Compound Ib.

What is claimed is:

1. A compound having the formula

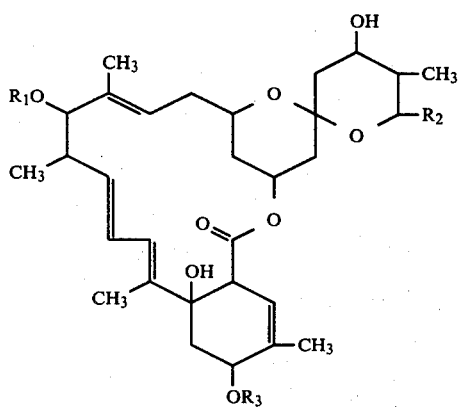

wherein:
(a.) $R_1$ is α-L-oleandrosyl; $R_2$ is sec-butyl; and $R_3$ is methyl;
(b.) $R_1$ is α-L-oleandrosyl; $R_2$ is sec-butyl; and $R_3$ is hydrogen; and
(c.) $R_1$ is α-L-oleandrosyl-α-L-oleandrosyl; $R_2$ is sec-butyl and $R_3$ is hydrogen.

2. The compound of claim 1 wherein $R_1$ is α-L-oleandrosyl; $R_2$ is sec-butyl; and $R_3$ is methyl.

3. The compound of claim 1 wherein $R_1$ is α-L-oleandrosyl; $R_2$ is sec-butyl; and $R_3$ is hydrogen.

4. The compound of claim 1 wherein $R_1$ is α-L-oleandrosyl-α-L-oleandrosyl; $R_2$ is sec-butyl and $R_3$ is hydrogen.

5. A compound having the formula:

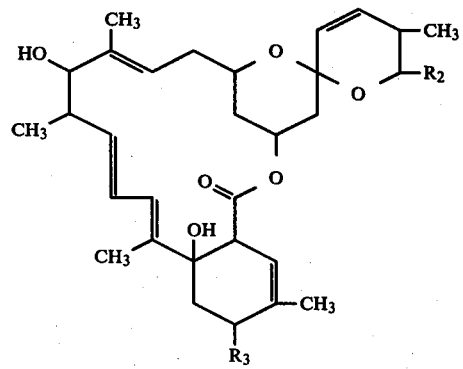

wherein:
(a.) $R_2$ is isopropyl; and $R_3$ is methoxy;
(b.) $R_2$ is sec-butyl; and $R_3$ is keto; and
(c.) $R_2$ is iso-propyl; and $R_3$ is keto.

6. The compound of claim 5 wherein $R_2$ is iso-propyl; and $R_3$ is methoxy.

7. The compound of claim 5 wherein $R_2$ is sec-butyl; and $R_3$ is keto.

8. The compound of claim 5 wherein $R_2$ is iso-propyl and $R_3$ is keto.

9. A compound having the formula:

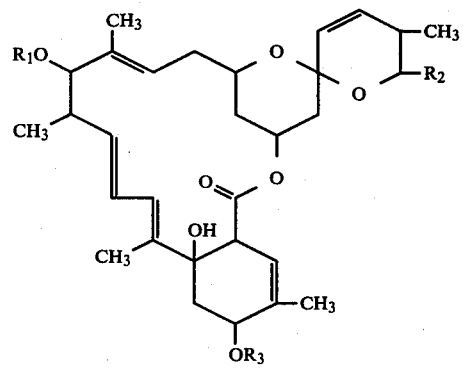

wherein $R_1$ is α-L-oleandrosyl-α-L-oleandrosyl; $R_2$ is sec-butyl; and $R_3$ is hydrogen.

10. A method for the treatment of parasite infections in animals infected with parasites, which comprises administering to said animal an effective amount of a compound of claims 1, 5 or 9.

11. A composition useful for the treatment of parasite infections which comprises an inert carrier and an effective amount of a compound of claims 1, 5 or 9.

* * * * *